United States Patent
Stemmler et al.

(10) Patent No.: US 9,765,002 B2
(45) Date of Patent: Sep. 19, 2017

(54) POLYTHIOLS AS CIS/TRANS ISOMERIZATION CATALYSTS FOR UNSATURATED COMPOUNDS

(71) Applicant: DSM IP ASSETS B.V., Heerlen (NL)

(72) Inventors: René Tobias Stemmler, Kaiseraugst (CH); Nadine Greiner, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/651,510

(22) PCT Filed: Dec. 18, 2013

(86) PCT No.: PCT/IB2013/061082
§ 371 (c)(1),
(2) Date: Jun. 11, 2015

(87) PCT Pub. No.: WO2014/097171
PCT Pub. Date: Jun. 26, 2014

(65) Prior Publication Data
US 2015/0315113 A1 Nov. 5, 2015

(30) Foreign Application Priority Data

Dec. 18, 2012 (EP) .................... 12197798

(51) Int. Cl.
C07C 43/313 (2006.01)
C07C 321/30 (2006.01)
C07C 45/67 (2006.01)
C07D 319/06 (2006.01)

(52) U.S. Cl.
CPC ............ *C07C 43/313* (2013.01); *C07C 45/67* (2013.01); *C07C 321/30* (2013.01); *C07D 319/06* (2013.01); *C07B 2200/09* (2013.01)

(58) Field of Classification Search
None
See application file for complete search history.

(56) References Cited

U.S. PATENT DOCUMENTS

| 4,028,385 | A | 6/1977 | Fujita et al. |
| 4,338,170 | A | 7/1982 | Murata et al. |
| 5,908,957 | A | 6/1999 | Wildermann |

FOREIGN PATENT DOCUMENTS

| CH | 620 891 | 12/1980 |
| JP | 51-29436 | 9/1974 |
| JP | 51-32511 | 3/1976 |
| JP | 55-167236 | 12/1980 |
| JP | 2016-503757 | 2/2016 |
| WO | 00/64959 | 11/2000 |

OTHER PUBLICATIONS

Official Action, CN Appln. No. 201380065876.8, Mar. 3, 2016.
Yanagisawa et al, *Double Alkylation of α,β-Unsaturated Acetals. An inverse Polarity Approach*, J.Am.Chem.Soc. 1989, 111, 366-368.
Mori et al, *Stereochemistry of Aplidiasphingosine as Proposed by the Assymetric Synthesis and $^{13}C$-NMR Study of Sphingosine Relatives*, Tetrahedron Letters, vol. 22, No. 44, pp. 4433-4436 (1981).
International Search Report for PCT/IB2013/061082 mailed Feb. 26, 2014, three pages.
Barrero et al, *First synthesis of achilleol A using titanium(III) chemistry*, Tetrahedron Letters 43 (2002) 2793-2796.
Justicia et al, *Palladium mediated C—H activation in the field of terpenoids: synthesis of rostratone*, Tetrahedron Letters 45 (2004) 4293-4296.
Sartori et al, *Protection (and Deprotection) of Functional Groups in Organic Synthesis by Heterogenous Catalysis*, Chem Rev. 2004, 104, 199-250.

*Primary Examiner* — Deepak Rao
*Assistant Examiner* — Laura Daniel
(74) *Attorney, Agent, or Firm* — Nixon & Vanderhye P.C.

(57) ABSTRACT

The present invention relates to a process of a cis/trans isomerization of an unsaturated compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid using polythiol as cis/trans isomerization catalyst. It has been observed that the isomerization is very efficient and fast.

22 Claims, 5 Drawing Sheets

POLYTHIOLS AS CIS/TRANS ISOMERIZATION CATALYSTS FOR UNSATURATED COMPOUNDS

This application is the U.S. national phase of International Application No. PCT/IB2013/061082 filed 18 Dec. 2013 which designated the U.S. and claims priority to EP 12197798.7 filed 18 Dec. 2012, the entire contents of each of which are hereby incorporated by reference.

TECHNICAL FIELD

The present invention relates to the cis/trans isomerization of unsaturated compounds.

BACKGROUND OF THE INVENTION

Unsaturated compounds have carbon-carbon double bonds. These compounds exist in either the cis or the trans configuration. Specifically unsaturated compounds having functional groups having C=O are technically very important and have different properties depending on which double bond isomer (cis or trans) is present in the corresponding compound. These compounds are particularly important for the fields of flavours and fragrances, pharmaceutical compositions and the synthesis of vitamins, particularly of vitamin K1 as well as tocopherols. The isomers particularly differ in odour as well as in their behaviour towards asymmetric additions to the respective carbon-carbon double bond.

It is known that carbon-carbon double bonds can be isomerized. Transition metal derivatives as well as sulphur compounds such as sulphides or disulfides or monomercaptanes are known to isomerize farnesol as described for example in DE 25 57 837.

U.S. Pat. No. 4,028,385 discloses transition metal catalysts as well as organic sulphur compounds such as sulphides or disulfides or monomercaptanes for the isomerization isomerize of farnesylacetic acids and esters as well as rectification of the corresponding stereoisomeric mixtures.

However, it has been observed that the organic sulphur compounds disclosed by the state of the art are not very efficient for the unsaturated compounds being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid.

SUMMARY OF THE INVENTION

Therefore, the problem to be solved by the present invention is to offer a process of isomerization and an isomerization catalyst which is very efficient, respectively, for compounds being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid.

Surprisingly, it has been found that a process according to the claims 1, 8 and 10 as well as the composition according to claim 16 is able to solve this problem. It has been found that polythiols are particularly suitable for the isomerization of the above mentioned compounds. They isomerize very efficiently the carbon-carbon double bond of these compounds. Due to the process of the invention it has become possible to have transformed essentially all of the undesired isomer into the desired isomer. This is not only possible in the case of a pure isomer but also in case of a mixture.

Further aspects of the invention are subject of further independent claims. Particularly preferred embodiments are subject of dependent claims.

BRIEF DESCRIPTION OF THE DRAWINGS

FIGS. 1a) and 1b) respectively show the results of isomerization and the stability behaviour according to a first series of experiments in the Examples below;

DETAILED DESCRIPTION OF THE INVENTION

In a first aspect the present invention relates to a process of a cis/trans isomerization of an unsaturated compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid comprising the steps a) providing a cis or a trans isomer of a unsaturated compound A;

b) adding a polythiol to the cis or trans isomer of the unsaturated compound A of step a);

c) heating the mixture of polythiol and cis or trans isomer of the unsaturated compound A to a temperature of between 20° C. and the boiling point of the unsaturated compound A, particularly between 50° C. and the boiling point of the unsaturated compound A;

leading to a mixture of cis/trans isomers of the unsaturated compound A.

The term "independently from each other" in this document means, in the context of substituents, moieties, or groups, that identically designated substituents, moieties, or groups can occur simultaneously with a different meaning in the same molecule.

Substance names starting with "poly" such as polythiol as used in the present document refer to substances formally containing two or more of the corresponding functional groups per molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

An "aromatic polythiol" is a polythiol which has two or more SH groups being bound directly to an aromatic hydrocarbon.

A "phenolic alcohol" means in this document an alcohol which has a hydroxyl group which is bound directly to an aromatic group.

The term "stereogenic centre" as used in this document is an atom, bearing groups such that interchanging of any two of the groups leads to a stereoisomer. Stereoisomers are isomeric molecules that have the same molecular formula and sequence of bonded atoms (constitution), but that differ in the three-dimensional orientations of their atoms in space.

The configuration at a stereogenic centre is defined to be either R or S. The R/S-concept and rules for the determination of the absolute configuration in stereochemistry is known to the person skilled in the art.

In the present document a carbon-carbon double bond is defined as being "prochiral" if addition of molecular hydrogen to said carbon-carbon double bond leads to the formation of a stereogenic carbon centre.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

A "cis/trans isomerization catalyst" is a catalyst which is able to isomerize a cis isomer (Z-isomer) to a cis/trans isomer mixture (E/Z isomer mixture) or to isomerize a trans isomer (E-isomer) to a cis/trans isomer (E/Z isomer mixture).

The terms "E/Z", "cis/trans" and "R/S" denote mixtures of E and Z, of cis and trans, and of R and S, respectively.

The term "isomerization" or "isomerize" is to be understood as being limited to cis/trans isomerization in the whole document.

An "equilibrium cis/trans ratio" is the ratio of a specific couple of cis and trans isomer which is achieved as a result of submitting either said cis or trans isomer to an isomerization using the process of this invention for an extended time, i.e. until no further change of the cis/trans ratio can be observed in time. Each pair of cis/trans isomers has a different equilibrium cis/trans ratio.

A "non-equilibrium cis/trans ratio" is any ratio of cis to trans isomer which differs from the "equilibrium cis/trans ratio".

An "unsaturated" compound, ketone, ketal, aldehyde, acetal, carboxylic acid, ester of an unsaturated carboxylic acid or amide of an unsaturated carboxylic acid is defined as to be a ketone, aldehyde, ketal, aldehyde, acetal, carboxylic acid, ester of an unsaturated carboxylic acid or amide of an unsaturated carboxylic acid which is olefinically unsaturated, i.e. that it has at least one carbon-carbon double bond in its chemical structure, and which preferably has at least one prochiral carbon-carbon double bond.

In case identical labels for symbols or groups are present in several formulae, in the present document, the definition of said group or symbol made in the context of one specific formula applies also to other formulae which comprises said same label.

In the present document any single dotted line represents the bond by which a substituent is bound to the rest of a molecule.

In the present document the boldface designations such as A or $I_{lbp}$ or $I_{hbp}$ are used in the present document only to improve readability and for identification.

Unsaturated Compound A

The unsaturated compound A, selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid, has at least one carbon-carbon double bond in its chemical structure and preferably has at least one prochiral carbon-carbon double bond.

It may have more than 1 prochiral carbon-carbon double bonds and/or 1 or more non-prochiral carbon-carbon double bond(s).

Preferably the unsaturated compound A is of formula (I-0A) or (I-0B) or (I-0C) or (I-0D) or (I-0E) or (I-0F)

wherein R' stands for a linear or a cycloaliphatic hydrocarbyl group which optionally contains additional carbon-carbon double bond(s) and Q' stands for a group selected of the group consisting of wherein $R^0$ stands for a $C_1$-$C_4$-alkyl group, particularly for a methyl group;
$Q^1$ and $Q^2$ stand for a $C_1$-$C_{10}$ alkyl group or a halogenated $C_1$-$C_{10}$ alkyl group; $C_1$-$C_4$-alkyl group or form together a $C_2$-$C_6$ alkylene group or a $C_6$-$C_8$ cycloalkylene group together;
R" stands for a $C_1$-$C_4$-alkyl group, particularly for a methyl or ethyl group; and
R'" stands for H or a $C_1$-$C_4$-alkyl group, particularly for a methyl or ethyl group;
and where a wavy line represents a carbon-carbon bond which is linked to the adjacent carbon-carbon double bond so as to have said carbon-carbon double bond either in the Z or in the E-configuration;

and wherein the double bond having dotted lines (=====) in formula (I-0B) or (I-0D) or (I-0F) represent either a single carbon-carbon bond or a double carbon-carbon bond.

In one embodiment, the formula (I-0A) or (I-0C) has a group R' of the formula and is preferably a methylketone or an ketal thereof, preferably alpha ionone, beta ionone, gamma ionone; alpha iso-ionone, beta iso-ionone, gamma iso-ionone; alpha normal-methylionone, beta normal-methylionone or gamma normal-methylionone; or an ketal thereof.

It is preferred that the unsaturated compound A is an unsaturated ketone or unsaturated ketal or an unsaturated aldehyde or an unsaturated acetal.

In one preferred embodiment the unsaturated compound A is an unsaturated ketone or ketal thereof or an unsaturated aldehyde or acetal thereof and has a carbon-carbon double bond in the γ,δ position relative to the carbonyl group.

In another preferred embodiment the unsaturated compound A is an unsaturated ketone or ketal thereof or an unsaturated aldehyde or acetal thereof and has a carbon-carbon double bond in the α,β position relative to the carbonyl group.

In a still another preferred embodiment the unsaturated compound A is an unsaturated ketone or ketal thereof or an unsaturated aldehyde or acetal thereof and has a carbon-carbon double bond in the α,β position relative to the carbonyl group and has a carbon-carbon double bond in the γ,δ position relative to the carbonyl group.

It is strongly preferred that that the unsaturated compound A is of formula (I) or (II)

wherein Q stands for H or CH$_3$ and m and p stand independently from each other for a value of 0 to 3 with the proviso that the sum of m and p is 0 to 3; and where a wavy line represents a carbon-carbon bond which is linked to the adjacent carbon-carbon double bond so as to have said carbon-carbon double bond either in the Z or in the E-configuration and where the substructures in formula (I) and (II) represented by s1 and s2 can be in any sequence;

and wherein the double bond having dotted lines (=====) in formula (I) and (II) represent either a single carbon-carbon bond or a double carbon-carbon bond;

and wherein ✧ represents a stereogenic centre.

The sum of m and p is preferably 0 to 2, particularly 0 or 1.

The unsaturated ketone or unsaturated aldehyde of formula (I) or (II), hence, can be an individual substance or a mixture of different stereoisomers having different orientation at the stereogenic centres marked by ✧ or at the double bond to which the wavy bond is attached. It is preferred, however, that the unsaturated ketone or unsaturated aldehyde of formula (I) or (II) is a single stereoisomer with specific configuration(s) at the stereogenic centres and double bonds. It is preferred that the configuration at the stereogenic centre(s) is the R-configuration. In case of p≥2, it is preferred that all the different stereogenic centres marked by ✧ in have the same configuration, i.e. all the S-configuration or all the R-configuration, preferably all in the R-configuration.

Particularly preferred unsaturated ketones or aldehydes have the formula (II). Most preferably the unsaturated ketone or aldehyde is selected from the group consisting of 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, (R)-6,10-dimethylundec-3-en-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the unsaturated ketone or aldehyde is a ketone.

It is, furthermore, preferred that the unsaturated compound A is a ketal or acetal of an unsaturated ketone or unsaturated aldehyde, particularly an acetal or a ketal of formula (I) or (II).

The formation of a ketal from a ketone, or of an acetal from an aldehyde, per se, is known to the person skilled in the art.

The ketal of an unsaturated ketone can be preferably formed from the above mentioned unsaturated ketone and an alcohol. The acetal of an unsaturated aldehyde can be formed from the above mentioned unsaturated aldehyde and an alcohol.

It is known to the person skilled in the art that there are alternative routes of synthesis for acetal or ketals. In principle, the ketal and acetals can also be formed by treating a ketone or an aldehyde with ortho-esters or by trans-ketalization such as disclosed for example in Pério et al., *Tetrahedron Letters* 1997, 38(45), 7867-7870, or in Lorette and Howard, *J. Org. Chem.* 1960, 25, 521-525, the entire content of both is hereby incorporated by reference.

Preferably the ketal or acetal is formed from the above mentioned unsaturated ketone or unsaturated aldehyde and an alcohol.

The alcohol used for the ketal or acetal formation can, principally, be any alcohol, i.e. the alcohol may comprise one or more hydroxyl groups. The alcohol may be a phenolic alcohol or an aliphatic or cycloaliphatic alcohol. Preferably, however, the alcohol has one hydroxyl group (=monol) or two hydroxyl groups (=diol).

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated $C_1$-$C_8$-alkyl alcohols, particularly 2,2,2-trifluoroethanol. Particularly suitable are primary or secondary alcohols. Preferably primary alcohols are used as alcohols with one hydroxyl group. Particularly methanol, ethanol, 1-propanol, 2-propanol, 1-butanol, 2-butanol or 2,2,2-trifluoroethanol, preferably methanol, ethanol, 1-propanol, 1-butanol or 2,2,2-trifluoroethanol, are used as alcohols with one hydroxyl group.

In another embodiment the alcohol is a diol. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)cyclohexanol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl groups are in one embodiment bound to two adjacent carbon atoms, hence these diols are vicinal diols. Vicinal diols form a 5 membered ring in a ketal or acetal.

Particularly suitable are vicinal diols which are selected from the group consisting of ethane-1,2-diol, propane-1,2-diol, butane-1,2-diol, butane-2,3-diol, 2-methylpropane-1,2-diol, benzene-1,2-diol and syn-cyclohexane-1,2-diol, particularly ethane-1,2-diol.

Other particularly suitable are diols, in which the hydroxyl groups are separated by 3 carbon atoms, and, hence, form a very stable 6 membered ring in a ketal or acetal. Particularly suitable diols of this type are propane-1,3-diol, butane-1,3-diol, 2-methylpropane-1,3-diol, 2-methylbutane-1,3-diol, 2,2-dimethylpropane-1,3-diol, 1,2-dimethylpropane-1,3-diol, 3-methylpentane-2,4-diol and 2-(hydroxymethyl)cyclohexanol.

Preferably primary alcohols are used as diols.

The reaction conditions and stoichiometry used for the acetal or ketal formation are known to the person skilled in the art. Particularly the acetal or ketal is formed under the influence of an acid.

The preferred ketal of an unsaturated ketone or the preferred acetal of an unsaturated aldehyde are of formula (XI) or (XII)

(XI)

(XII)

The groups and symbols in formula (XI) and (XII) have the same meaning as defined before in this document for formula (I) and (II).

$Q^1$ and $Q^2$ stand either individually both for a $C_1$-$C_{10}$ alkyl group or a halogenated $C_1$-$C_{10}$ alkyl group;

or form together a $C_2$-$C_6$ alkylene group or a $C_6$-$C_8$ cycloalkylene group.

$Q^1$ and $Q^2$ stand particularly for either a linear $C_1$-$C_{10}$ alkyl group or fluorinated linear $C_1$-$C_{10}$ alkyl group, preferably a linear $C_1$-$C_4$ alkyl group or a —$CH_2CF_3$ group or a group of formula in which $Q^3$, $Q^4$, $Q^5$ and $Q^6$ are independently from each other hydrogen atoms or methyl or ethyl groups.

Preferably the ketal or the acetal of formula (XI) or (XII) are (E)-2-(4,8-dimethylnona-3,7-dien-1-yl)-2,5,5-trimethyl-1,3-dioxane, (E)-2,6-dimethyl-10,10-bis(2,2,2-trifluoroethoxy)undeca-2,6-diene, (E)-2-(4,8-dimethylnon-3-en-1-yl)-2,5,5-trimethyl-1,3-dioxane, (E)-6,10-dimethyl-2,2-bis(2,2,2-trifluoroethoxy)undec-5-ene, (E)-2,5,5-trimethyl-2-(4,8,12-trimethyltridec-3-en-1-yl)-1,3-dioxane, (R,E)-2,5,5-trimethyl-2-(4,8,12-trimethyltridec-3-en-1-yl)-1,3-dioxane, (E)-6,10,14-trimethyl-2,2-bis(2,2,2-trifluoroethoxy)pentadec-5-ene, (R,E)-6,10,14-trimethyl-2,2-bis(2,2,2-trifluoroethoxy)pentadec-5-ene, (Z)-2-(4,8-dimethylnona-3,7-dien-1-yl)-2,5,5-trimethyl-1,3-dioxane, (Z)-2,6-dimethyl-10,10-bis(2,2,2-trifluoroethoxy)-undeca-2,6-diene, (Z)-2-(4,8-dimethylnon-3-en-1-yl)-2,5,5-trimethyl-1,3-dioxane, (Z)-6,10-dimethyl-2,2-bis(2,2,2-trifluoroethoxy)undec-5-ene, (Z)-2,5,5-trimethyl-2-(4,8,12-trimethyltridec-3-en-1-yl)-1,3-dioxane, (R,Z)-2,5,5-trimethyl-2-(4,8,12-trimethyltridec-3-en-1-yl)-1,3-dioxane, 2,5,5-trimethyl-2-((3E,7E)-4,8,12-trimethyltrideca-3,7,11-trien-1-yl)-1,3-dioxane, (6E,10E)-2,6,10-trimethyl-14,14-bis(2,2,2-tri-fluoroethoxy)pentadeca-2,6,10-triene, 2,5,5-trimethyl-2-((3E,7E)-4,8,12-trimethyltrideca-3,7-dien-1-yl)-1,3-dioxane, (5E,9E)-6,10,14-trimethyl-2,2-bis(2,2,2-trifluoro-ethoxy)pentadeca-5,9-diene, 2,5,5-trimethyl-2-((3Z,7E)-4,8,12-trimethyltrideca-3,7,11-trien-1-yl)-1,3-dioxane, 2,5,5-trimethyl-2-((3E,7Z)-4,8,12-trimethyltrideca-3,7,11-trien-1-yl)-1,3-dioxane, 2,5,5-trimethyl-2-((3Z,7Z)-4,8,12-trimethyltrideca-3,7,11-trien-1-yl)-1,3-dioxane, (6Z,10E)-2,6,10-trimethyl-14,14-bis(2,2,2-trifluoro-ethoxy)pentadeca-2,6,10-triene, (6E,10Z)-2,6,10-trimethyl-14,14-bis(2,2,2-tri-fluoroethoxy)pentadeca-2,6,10-triene, (6Z,10Z)-2,6,10-trimethyl-14,14-bis(2,2,2-tri-fluoroethoxy)pentadeca-2,6,10-triene, 2,5,5-trimethyl-2-((3Z,7E)-4,8,12-trimethyltrideca-3,7-dien-1-yl)-1,3-dioxane, 2,5,5-trimethyl-2-((3E,7Z)-4,8,12-trimethyltrideca-3,7-dien-1-yl)-1,3-dioxane, 2,5,5-trimethyl-2-((3Z,7Z)-4,8,12-trimethyltrideca-3,7-dien-1-yl)-1,3-dioxane, (5Z,9E)-6,10,14-trimethyl-2,2-bis(2,2,2-trifluoroethoxy)pentadeca-5,9-diene, (5E,9Z)-6,10,14-trimethyl-2,2-bis(2,2,2-trifluoroethoxy)pentadeca-5,9-diene, (5Z,9Z)-6,10,14-trimethyl-2,2-bis(2,2,2-trifluoroethoxy)pentadeca-5,9-diene, (E)-2-(2,6-dimethylhept-1-en-1-yl)-5,5-dimethyl-1,3-dioxane, (E)-3,7-dimethyl-1,1-bis(2,2,2-trifluoroethoxy)oct-2-ene, (E)-3,7-dimethyl-1,1-bis(2,2,2-trifluoroethoxy)octa-2,6-diene, (Z)-2-(2,6-dimethylhept-1-en-1-yl)-5,5-dimethyl-1,3-dioxane, (Z)-3,7-dimethyl-1,1-bis(2,2,2-trifluoro-ethoxy)oct-2-ene, (Z)-3,7-dimethyl-1,1-bis(2,2,2-trifluoroethoxy)octa-2,6-diene, 2,6-dimethyl-8,8-bis(2,2,2-trifluoroethoxy)oct-2-ene, (R)-2,6-dimethyl-8,8-bis(2,2,2-trifluoroethoxy)oct-2-ene, 2-((1Z,3E)-4,8-dimethylnona-1,3,7-trien-1-yl)-2,5,5-trimethyl-1,3-dioxane, 2-((1E,3Z)-4,8-dimethylnona-1,3,7-trien-1-yl)-2,5,5-trimethyl-1,3-dioxane, 2-((1Z,3Z)-4,8-dimethylnona-1,3,7-trien-1-yl)-2,5,5-trimethyl-1,3-dioxane, (6Z,8E)-2,6-dimethyl-10,10-bis(2,2,2-trifluoroethoxy)undeca-2,6,8-triene, (6E,8Z)-2,6-dimethyl-10,10-bis(2,2,2-trifluoroethoxy)undeca-2,6,8-triene, (6Z,8Z)-2,6-dimethyl-10,10-bis(2,2,2-trifluoroethoxy)undeca-2,6,8-triene, (Z)-2,5-dimethyl-2-(4,8,12-trimethyltridec-3-en-1-yl)-1,3-dioxane, (R,Z)-2,5-dimethyl-2-(4,8,12-trimethyltridec-3-en-1-yl)-1,3-dioxane, (Z)-6,10,14-trimethyl-2,2-bis(2,2,2-trifluoroethoxy)pentadec-5-ene and (R,Z)-6,10,14-trimethyl-2,2-bis(2,2,2-trifluoroethoxy)pentadec-5-ene, In step a) a cis or a trans isomer of an unsaturated compound A is provided.

In one embodiment only one single stereoisomer of the compound A is provided. Such a single stereoisomer of compound A may be a result of a stereospecific synthesis or of a separation process of stereoisomers.

In another embodiment the cis or a trans isomer of a unsaturated compound A is provided as a mixture of cis and trans isomers in a non-equilibrium cis/trans ratio. Typically such a non-equilibrium cis/trans ratio is larger than 70/30, preferably larger than 80/20, more preferably larger than 90/10 or smaller than 30/70, preferably smaller than 20/80, more preferably smaller than 10/90.

Polythiol

In step b) a polythiol is added to the cis or trans isomer of the unsaturated compound A of step a);

The polythiol is a cis/trans isomerization catalyst which isomerizes the carbon carbon double bond(s).

It is important to note that we have observed that thiols having only 1 mercapto group (i.e. monothiols) cannot be used as cis/trans isomerization catalyst for the unsaturated compounds A or show only very poor efficiency as compared to polythiols.

Particularly suitable as polythiols are aromatic polythiols or polythiols of formula (X)

wherein n1 represents an integer from 1 to 4, particularly 2, and m1 represents an integer from 2 to 8, particularly 3 or 4, preferably 4;

and A represents an aliphatic m1-valent hydrocarbon group of the molecular weight of between 28 g/mol and 400 g/mol, particularly between 90 and 150 g/mol.

A first group of preferred polythiols are aromatic polythiols. The SH groups are bound directly on an aromatic hydrocarbon. The aromatic hydrocarbon may have one or several aromatic rings. The aromatic rings can form a fused ring system or can be separated by spacers for example by alkylene groups or by functional groups. The SH groups may be bound directly on a the same aromatic ring or on different aromatic rings.

Particularly preferred as aromatic polythiols are 4,4'-dimercaptobiphenyl or 4,4'-thiodibenzenethiol.

A further group of preferred polythiols are polythiols of formula (X).

These substances are esters of a polyol $A(OH)_{m1}$ and a carboxylic acid having a terminal mercapto group SH—$(CH_2)_{n1}$—COOH. The preferred polyols $A(OH)_{m1}$ having a molecular weight of between 62 and 538 are trimethylolpropane, trimethylolethane, trimethylolmethane, tripropylene glycol, 1,2-propanediol, isomers of 1,4-butanediol, isomers of 1,5-pentanediol, isomers of 1,6-hexanediol, dipropylene glycol, 1,4-cyclohexanedimethanol and isomers, 1,4-bis(2-hydroxyethoxy)cyclohexane, decamethyleneglycol, norbornyleneglycol, 1,4-benzenediethanol, 2,4-dimethyl-2-ethylenehexane-1,3-diol, 2-butene-1,4-diol, ethoxylated trimethylolpropane, trimethylolhexane, 1,2,4-butanetriol, pentaerythritol, di pentaerythritol (=2,2'-(oxybis(methylene))bis(2-(hydroxymethyl)-propane-1,3-diol)), di(trimethylolpropane) (=2,2'-(oxybis(methylene))bis(2-ethylpropane-1,3-diol)), di(trimethylolethane) (=2,2'-(oxybis(methylene))bis(2-methylpropane-1,3-diol)), ethyleneglycol, diethyleneglycol, dipropyleneglycol.

The person skilled in the art is aware that the above esters can be prepared by different methods, not limited of a reaction of the polyol with the above mentioned carboxylic acid having a terminal mercapto group.

The polythiols pentaerythritol tetra(mercaptoacetate), trimethylolpropane tris(mercaptoacetate), glycol dimercaptoacetate, pentaerythritol tetra-(3-mercaptopropionate), trimethylolpropanetri-(3-mercaptopropionate)(=2-ethyl-2-(((3-mercaptopropanoyl)oxy)methyl)propane-1,3-diyl bis (3-mercaptopropanoate)) and glycol di-(3-mercaptopropionate) have been shown to be highly preferred polythiols of formula (X) and are the preferred polythiols of all the above mentioned polythiols.

The use of polythiols of formula (X) as cis/trans isomerization catalysts is very advantageous in that polythiols have generally very low vapor pressures (i.e. high boiling points) allowing them to be used at elevated temperatures, e.g. while distilling the low boiling isomer. Furthermore, the polythiols bear a high density of thiol-functionalities per molecular weight, which is very advantageous, in that only little catalyst needs to be added.

The use of polythiol as cis/trans isomerization catalysts is very advantageous as they allow a very fast isomerization.

The amount of a polythiol added to the cis or trans isomer of the unsaturated compound A is preferably between 1 and 20%, particularly between 3 and 5%, by weight in relation to the amount of the unsaturated compound A.

In view of molar ratio, it is preferred that the molar ratio of polythiol and the unsaturated compound A is between 1/100 and 20/100, particularly between 1/100 and 4/100.

The way of adding of the polythiol to the unsaturated compound A is uncritical and can be done as needed. It can be added before or during step c).

Isomerization

In step c) the mixture of polythiol and cis or trans isomer of the unsaturated compound A is heated to a temperature of between 20° C. and the boiling point of the unsaturated compound A, particularly between 50° C. and the boiling point of the unsaturated compound A. In the present document the "boiling point of the unsaturated compound A" is defined as being the boiling point of the lowest boiling cis or trans isomers being formed by the process.

Under the action of the polythiol and temperature the cis and/or trans isomers of the unsaturated compound A isomerize. The ratio of cis and trans isomers being formed by the isomerization converges over time gradually to an equilibrium, e.g. the equilibrium cis/trans ratio. This equilibrium cis/trans ratio is a specific value which is different for each unsaturated compound A.

It has been observed that the rate of isomerization is strongly depending on the polythiol and that polythiol are much faster than monothiols. Furthermore it has been observed that the polythiols lead to less degradation of the unsaturated compound A at elevated temperatures as compared to the monothiols.

It further has been observed that addition of polar solvents such as amides, pyrrolidones, sulfones, sulfoxides, ionic liquids, particularly N,N-dimethylformide (DMF) or N-methyl-2-pyrrolidone (NMP), sulfolane, dimethylsulfoxide (DMSO) and 1-butyl-3-methylimidazolium bromide has an accelarating effect on the isomerization.

Therefore, it is preferred that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP), sulfolane and dimethylsulfoxide (DMSO).

More preferred it is that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP) and dimethylsulfoxide (DMSO).

The isomerization of a cis or of a trans isomer of an unsaturated compound A is very interesting because very often one of the isomers is the isomer of interest. The cis and trans isomers mostly have different properties. For example core properties of interest such as odour or reactivity in specific chemical reactions is strongly different for the trans as compared to the cis isomer. In case of citral the trans isomer, geranial (=(E)-3,7-dimethylocta-2,6-dienal), has a strong lemon odour, whereas the cis isomer, neral (=(Z)-3,7-dimethylocta-2,6-dienal), has a lemon odour which is less intense, but sweeter. On the other hand if the unsaturated compound A has prochiral carbon-carbon double bond(s) the prochiral carbon-carbon double bond may lead to the formation of a chiral compound of a specific stereoisomeric configuration. For example an asymmetric hydrogenation of unsaturated compound A leads to the formation of stereogenic centre of the R or S configuration.

The isomerization offers the unique possibility of transforming at least a part of the undesired isomer into the desired isomer (=isomer of interest). On performing the method of isomerization and isolation in an optimal way, it even can be achieved that essentially all of the undesired isomer(s) can be transformed into the desired isomer(s) starting from a undesired isomer or a mixture of desired and undesired cis/trans isomers. More details for this possibility are given later in this document.

The above described process of a cis/trans isomerization of an unsaturated compound A leads to a mixture of cis/trans isomers of the unsaturated compound A.

From this mixture an isomer, the desired isomer, can be isolated. As the cis and trans isomers have different boiling points the favourite method of isolation is distillation. In order to minimize thermal degradation of the isomers it is advisable to distil under reduced pressure and by means of a distillation column. Very often the boiling points are very similar, however, by using specific distillation techniques and equipment it is nevertheless possible to separate or at least to enrich the desired isomer.

As not always the lowest boiling isomer is the one of interest there need to be principally two different processes of interest which are described in the following.

In case the lowest boiling isomer is the one of interest, in a further aspect the invention relates to a process of producing a specific cis isomer, respectively a specific trans isomer, of an unsaturated compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid from a mixture of cis and trans isomers thereof comprising the steps i) providing a mixture of cis isomer(s) in an amount of weight $w_{cis}$ and of trans isomer(s) in an amount of weight $w_{trans}$ of the unsaturated compound A;

ii) adding a polythiol iii) heating the mixture to a temperature $T_{iso1}$, which is the boiling point of that isomer $I_{lbp}$ which has the lowest boiling point of the mixture of the cis/trans isomers of step i);

iv) distilling off the isomer $I_{lbp}$ and collecting the isomer $I_{lbp}$;

v) cis/trans isomerization of the isomer(s) $I_{hbp}$ having a higher boiling point than the isomer $I_{lbp}$ in the presence of the polythiol being added in step ii);

wherein after the step v) the steps iii) and iv) and v) are repeated subsequently and wherein the weight of the collected isomer $I_{lbp}$ is more than $w_{cis}$ in case the collected isomer $I_{lbp}$ is a cis isomer of said unsaturated compound A;

or more than $w_{trans}$ in case the collected isomer $I_{lbp}$ is a trans isomer of said unsaturated compound A;

and wherein weight $w_{cis}$ and weight $w_{trans}$ are each 0 gram to 10 tons, with the proviso that the ratio of $w_{cis}$ and $w_{trans}$ is larger than 70/30 or smaller than 30/70 with the proviso that not both $w_{cis}$ and $w_{trans}$ are 0 grams.

In this process a mixture of cis isomer(s) in an amount of weight $w_{cis}$ and of trans isomer(s) in an amount of weight $w_{trans}$ of the unsaturated compound A is provided in step i). Because the weight $w_{cis}$ of the cis isomer(s) or the weight $w_{trans}$ of the trans isomer(s) is 0 grams to 10 tons with the proviso that not both $w_{cis}$ and $w_{trans}$ are 0 grams, a "mixture" in this context applies also to a single stereoisomer and not only to real isomer mixtures.

In a preferred embodiment both weight $w_{cis}$ and weight $w_{trans}$ are different from 0 grams, so that in the mixture provided in step i) the cis and trans isomer(s) of the unsaturated compound A are both physically present.

In this process the isomer of interest, i.e. the desired isomer, is the isomer $I_{lbp}$ which is the isomer having the lowest boiling point of the mixture of the cis/trans isomers provided in step i).

This isomer $I_{lbp}$ is isolated and separated by distillation and is collected in step iv).

In order to optimize purity, the distillation is made by using specific distillation techniques assuring that impurities by other isomers are as little as possible. This particularly is also achieved in that only a part, namely the purest fractions, of the desired isomer is collected in a distillation whereas a remainder is left in the distillation flask In order to optimize the yield of the desired isomer, the isomer(s) $I_{hbp}$ having a higher boiling point than the isomer $I_{lbp}$ are cis/trans isomerized in the presence of the polythiol (being added in step ii) in step v).

In the case, which is even the preferred case, where only a part of the isomer(s) $I_{lbp}$ are distilled and collected in step iv) the remainder of the distillation comprises still isomer(s) $I_{lbp}$. In this case, in step v) the cis/trans isomerization is done of the remainder of the distillation.

The isomer(s) $I_{hbp}$ and/or the remainder of the distillation is either isomerized continuously or batchwise isomerized in the presence of the polythiol. As by removal of desired product the remainder of the distillation is enriched in the undesired isomer to a non-equilibrium cis/trans ratio, the system adjusts according to Le Chatelier's principle and searches to achieve the equilibrium cis/trans ratio by transforming (i.e. isomerizing) the non-desired isomer into the desired isomer facilitated by the polythiol, the cis/trans isomerization catalyst. By repeating the steps steps iii) and iv) and v) after step v) subsequently it is assured that the yield is increased. The overall yield in the desired isomer isomer $I_{lbp}$ is heavily depending on the number of repetitions and/or the separation efficiency by the distillation.

The process leads to a net transformation of the undesired isomer to the desired isomer, which means in other words, that the weight of the collected isomer $l_{lbp}$ is more than $w_{cis}$ in case the collected isomer $I_{lbp}$ is a cis isomer of said unsaturated compound A;

or is more than $w_{trans}$ in case the collected isomer $I_{lbp}$ is a trans isomer of said unsaturated compound A;

when in the original mixture of cis and trans isomers of the unsaturated compound A provided in step a) the cis isomer(s) has a weight $w_{cis}$ and the trans isomer(s) has a weight $w_{trans}$.

As discussed, principally essentially all of the undesired isomer can be transformed into the desired isomer.

Hence, it is preferred that the weight of the collected isomer $I_{lbp}$ isomer is more than 80% by weight, preferably more than 90% by weight, of the sum of $w_{trans}$ and $w_{cis}$.

In case the higher boiling isomer is the one of interest, in a further aspect the invention relates to a process of producing a specific cis isomer, respectively a specific trans isomer, of an unsaturated compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid from a mixture of cis and trans isomers thereof comprising the steps a) providing a mixture of cis isomer(s) in an amount of weight $w_{cis}$ and of trans isomer(s) in an amount of weight $w_{trans}$ of the unsaturated compound A;
b) adding a polythiol
c) heating the mixture to a temperature $T_{iso1}$, which is the boiling point of that isomer $I_{lbp}$ which has the lowest boiling point of the mixture of the cis/trans isomers of step a);
d) distilling off the isomer $I_{lbp}$
e) isolating the specific isomer $I_{hbp}$ which has a higher boiling point than the isomer $I_{lbp}$ from the remainder of step d) and collecting the isomer $I_{hbp}$;
f) cis/trans isomerization of the isomer(s) $I_{lbp}$ and the remainder of step e) in case there is a remainder after step e) in the presence of polythiol being added in step b);
wherein after the step f) the steps c) and d) and e) and f) are repeated subsequently
and wherein the weight of the collected isomer $I_{hbp}$ is
more than $w_{cis}$ in case the collected isomer $I_{hbp}$ is a cis isomer of said unsaturated compound A;

or
more than $w_{trans}$ in case the collected isomer $I_{lbp}$ is a trans isomer of said unsaturated compound A;
and wherein weight $w_{cis}$ and weight $w_{trans}$ are each 0 gram to 10 tons, with the proviso that the ratio of $w_{cis}$ and $w_{trans}$ is larger than 70/30 or smaller than 30/70 with the proviso that not both $w_{cis}$ and $w_{trans}$ are 0 grams.

In this process a mixture of cis isomer(s) in an amount of weight $w_{cis}$ and of trans isomer(s) in an amount of weight $w_{trans}$ of the unsaturated compound A is provided in step a). Because the weight $w_{cis}$ of the cis isomer(s) or the weight of the $w_{trans}$ of the trans isomer(s) is in 0 grams to 10 tons with the proviso that not both $w_{cis}$ and $w_{trans}$ are 0 grams, a "mixture" in this context applies also to a single stereoisomer and not only to real isomer mixtures.

In a preferred embodiment both weight $w_{cis}$ and weight $w_{trans}$ are different from 0 grams, so that in the mixture provided in step a) the cis and trans isomer(s) of the unsaturated compound A are both physically present.

In this process the isomer of interest, i.e. the desired isomer $I_{hbp}$ which has a higher boiling point than the isomer $I_{lbp}$ which is the isomer having the lowest boiling point of the mixture of the cis/trans isomers provided in step a).

The lowest boiling isomer $I_{lbp}$ is distilled off in step d).

The specific isomer $I_{lbp}$ which has a higher boiling point than the isomer $I_{lbp}$ is isolated from the remainder of the distillation of step d) and is collected in step e).

Figure 1:
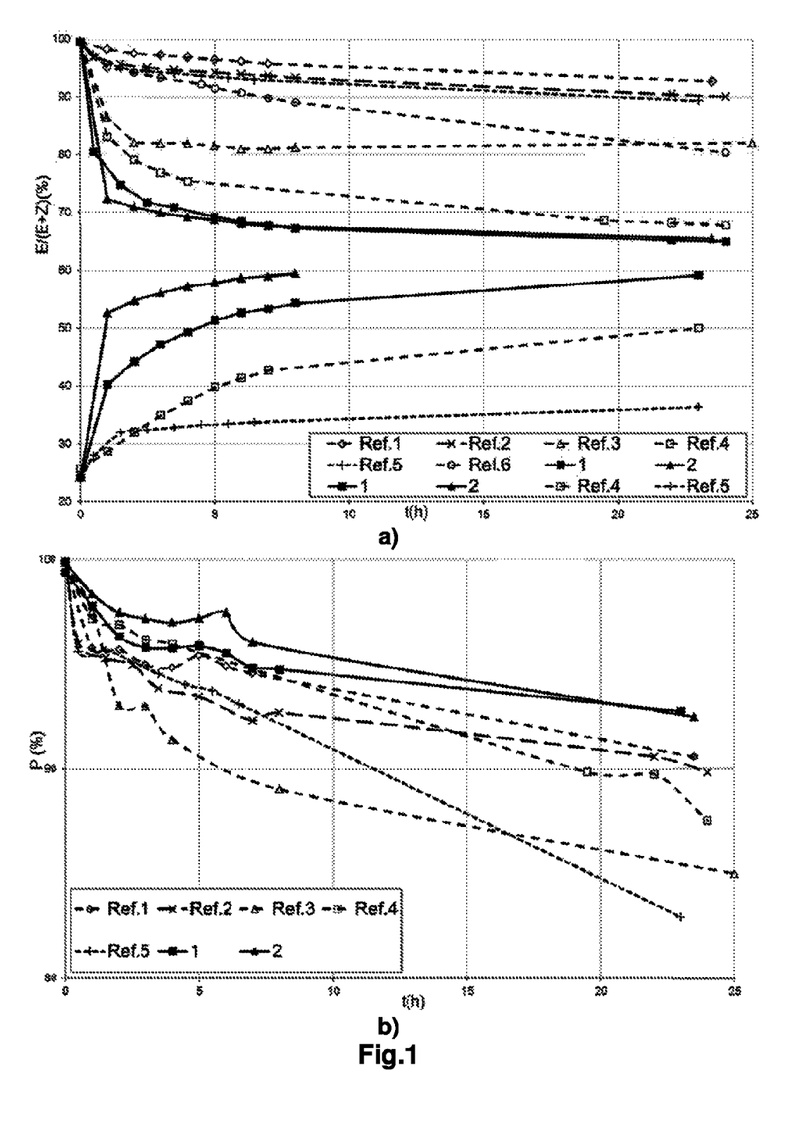

The isolation of the separation specific isomer $I_{lbp}$ is preferably done by specific distillation techniques, for example using a side take-off point at a rectification column and eventually further rectification of the material collected at said side take-off, such as the technique and equipment that has been disclosed for example in EP 2 269 998 A2, particularly FIGS. 1 and 3, the entire content of which is hereby incorporated by reference.

In order to optimize purity of the isomer $I_{hbp}$ the distillation in step d) and e) are made by using specific distillation techniques assuring that impurities by other isomers are as little as possible. This particularly is also achieved in that only a part, namely the purest fractions, of the desired isomer $I_{hbp}$ is collected in a distillation whereas the other fractions are combined with the remainder which is left in the distillation flask, and the lowest boiling isomer $I_{lbp}$ being distilled off in step d).

In step f) the isomer(s) $I_{lbp}$ and the remainder of step e) in case there is a remainder after step e) is isomerized in the presence of polythiol being added in step b).

In the case, which is even the preferred case, where only a part of the isomer(s) $I_{hbp}$ are isolated and collected in step e) the remainder of the distillation comprises still isomer(s) $I_{hbp}$.

The isomer $I_{lbp}$ and the remainder of step e) are either isomerized continuously or batchwise in the presence of the polythiol. As by removal of desired product the remainder of the distillation is enriched in the undesired isomer to a non-equilibrium cis/trans ratio, the system adjusts according to Le Chatelier's principle and searches to achieve the equilibrium cis/trans ratio by transforming (i.e. isomerizing) the non-desired isomer into the desired isomer facilitated by the polythiol, the cis/trans isomerization catalyst. By repeating the steps steps c) and d) and e) and f) after step f) subsequently it is assured that the yield is increased. The overall yield in the desired isomer isomer $I_{hbp}$ is heavily depending on the number of repetitions and/or the separation efficiency by the distillation.

The process leads to a net transformation of the undesired isomer to the desired isomer, which means in other words, that the weight of the collected isomer $I_{hbp}$ is more than $w_{cis}$ in case the collected isomer $I_{hbp}$ is a cis isomer of said unsaturated compound A;

or is more than $w_{trans}$ in case the collected isomer $I_{hbp}$ is a trans isomer of said unsaturated compound A;

when in the original mixture of cis and trans isomers of the unsaturated compound A provided in step a) the cis isomer(s) has a weight $w_{cis}$ and the trans isomer(s) has a weight $w_{trans}$.

As discussed, principally essentially all of the undesired isomer can be transformed into the desired isomer.

Hence, it is preferred that the weight of the collected isomer $I_{hbp}$ isomer is more than 80% by weight, preferably more than 90% by weight, of the sum of $w_{trans}$ and $w_{cis}$.

In both processes of producing a specific cis isomer, respectively a specific trans isomer, of an unsaturated compound A discussed in the previous paragraphs, it is preferred that the amount of polythiol is between 1 and 20% by weight, particularly between 3 and 5% by weight, in relation to the amount of the unsaturated compound A.

Furthermore, it is preferred the molar ratio of the polythiol and the unsaturated compound A is between 1/100 and 20/100, particularly between 1/100 and 4/100.

It further has been observed that addition of polar solvents such as amides, pyrrolidones, sulfones, sulfoxides, ionic liquids, particularly N,N-dimethylformide (DMF) or N-methyl-2-pyrrolidone (NMP), sulfolane, dimethylsulfoxide (DMSO) and 1-butyl-3-methylimidazolium bromide has an accelarating effect on the isomerization.

Therefore, it is preferred that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP), sulfolane and dimethylsulfoxide (DMSO).

More preferred it is that the process of a cis/trans isomerization is undertaken in the presence of a polar solvent, particularly a polar solvent which is selected from the group consisting of ionic liquids, particularly 1-butyl-3-methylimidazolium bromide, N,N-dimethylformide (DMF), N-methyl-2-pyrrolidone (NMP) and dimethylsulfoxide (DMSO).

Furthermore, it is preferred that in the process of a cis/trans isomerization the polythiol is of formula (X), as has been described before in detail.

In a further aspect the invention relates to composition comprising a polythiol and an unsaturated compound A of the formula (I) or (II).

The polythiol and the unsaturated compound A of the formula (I) or (II) as well as their ratio and their preferred embodiments have been discussed already before in detail in this document.

It is preferred that said composition further comprises at least one polar solvent, particularly at least one polar solvent which is selected from the group consisting of ionic liquids, particularly 1-butyl-3-methylimidazolium bromide, N,N-dimethylformide (DMF), N-methyl-2-pyrrolidone (NMP), sulfolane and dimethylsulfoxide (DMSO).

It is preferred that said composition further comprises at least one polar solvent, particularly at least one polar solvent which is selected from the group consisting of ionic liquids, particularly 1-butyl-3-methylimidazolium bromide, N,N-dimethylformide (DMF), N-methyl-2-pyrrolidone (NMP) and dimethylsulfoxide (DMSO).

In a further aspect the invention relates to a ketal or acetal which is selected from the group consisting of 2-(4,8-dimethylnona-3,7-dien-1-yl)-2,5,5-trimethyl-1,3-dioxane, 2,6-dimethyl-10,10-bis(2,2,2-trifluoroethoxy)undeca-2,6-diene, 2-(4,8-dimethylnon-3-en-1-yl)-2,5,5-trimethyl-1,3-dioxane, 6,10-dimethyl-2,2-bis(2,2,2-trifluoroethoxy)undec-5-ene, 2,5,5-trimethyl-2-(4,8,12-trimethyltridec-3-en-1-yl)-1,3-dioxane, (R)-2,5,5-trimethyl-2-(4,8,12-trimethyltridec-3-en-1-yl)-1,3-dioxane, 6,10,14-trimethyl-2,2-bis(2,2,2-trifluoroethoxy)pentadec-5-ene, (R)-6,10,14-trimethyl-2,2-bis(2,2,2-trifluoroethoxy)pentadec-5-ene, 2,5,5-trimethyl-2-(4,8,12-trimethyltrideca-3,7,11-trien-1-yl)-1,3-dioxane, 2,6,10-trimethyl-14,14-bis(2,2,2-trifluoroethoxy)pentadeca-2,6,10-triene, 2,5,5-trimethyl-2-(4,8,12-trimethyltrideca-3,7-dien-1-yl)-1,3-dioxane, 6,10,14-trimethyl-2,2-bis(2,2,2-trifluoro-ethoxy)pentadeca-5,9-diene, 2-(2,6-dimethylhept-1-en-1-yl)-5,5-dimethyl-1,3-dioxane, 3,7-dimethyl-1,1-bis(2,2,2-trifluoroethoxy)oct-2-ene, 3,7-dimethyl-1,1-bis(2,2,2-trifluoroethoxy)octa-2,6-diene, 2,6-dimethyl-8,8-bis(2,2,2-trifluoroethoxy)-oct-2-ene, (R)-2,6-dimethyl-8,8-bis(2,2,2-trifluoroethoxy)oct-2-ene, 2-(4,8-dimethylnona-1,3,7-trien-1-yl)-2,5,5-trimethyl-1,3-dioxane, 2,6-dimethyl-10,10-bis(2,2,2-trifluoroethoxy)undeca-2,6,8-triene, 2,5-dimethyl-2-(4,8,12-trimethyltridec-3-en-1-yl)-1,3-dioxane, (R)-2,5-dimethyl-2-(4,8,12-trimethyltridec-3-en-1-yl)-1,3-dioxane, 6,10,14-trimethyl-2,2-bis(2,2,2-trifluoroethoxy)pentadec-5-ene and (R)-6,10,14-trimethyl-2,2-bis(2,2,2-trifluoroethoxy)pentadec-5-ene as well as all their possible E/Z-isomers.

These ketals and acetals are particularly suited for being isomerized according to the process of the invention.

Finally, in a further aspect the invention relates to the use of a polythiol as catalyst for the cis/trans isomerization of an unsaturated compound A which is selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid. This use has been discussed already before in this document in detail.

EXAMPLES

The present invention is further illustrated by the following experiments.

In a first series of experiments the isomers of 6,10-dimethylundeca-5,9-dien-2-one have been separated by distillation. The E-isomer has been isolated as having a content of (E)-6,10-dimethylundeca-5,9-dien-2-one of 99.5% (determined by GC) and the Z-isomer has been isolated in an enriched fraction having a content of (Z)-6,10-dimethylundeca-5,9-dien-2-one of 75.4% and a content of (E)-6,10-dimethylundeca-5,9-dien-2-one of 24.1% (total 99.5% isomers, determined by GC).

The catalysts of table 1 were added to the E or Z isomer in an amount of 5% by weight (concentration related to ketone). Then the mixture was stirred and heated up to 140° C. under argon under which conditions isomerization took place. The amount of E and Z isomers was measured by GC regularly after certain reaction times.

TABLE 1

Catalysts used for the isomerization of (E)- and (Z)-6,10-dimethylundeca-5,9-dien-2-one, respectively, in FIG. 1.

| Example | Catalyst |
|---|---|
| Ref. 1 | 2,4,6-trimethylbenzenethiol |
| Ref. 2 | 2,3,4,5,6-pentachlorobenzenethiol |
| Ref. 3 | 2-mercaptoethanol |
| Ref. 4 | Thiophenol |
| Ref. 5 | Phenyldisulfide |
| Ref. 6 | 2-methylbenzenethiol |
| 1 | 4,4'-Dimercaptobiphenyl |
| 2 | pentaerythritol tetrakis (3-mercaptopropionate) |

FIG. 1a) shows the result of these isomerization experiments. The x-axis represents the time of heating, i.e. time of isomerization at 140° C., and the y-axis represents the percentage of E-isomer of the sum of isomers (E/(E+Z)) measured in the sample. For example a E/(E+Z) value of 80% represents a E/Z ratio of 80:20. FIG. 1a) shows that all catalysts induce an isomerization, i.e. the curves decrease in the case of the E-isomer with time and increase in case of the Z-isomer in time. The FIG. 1a) further shows that the polythiols (examples 1 and 2 (solid line) lead to much faster isomerization than the monothiols (Examples Ref. 1 to Ref. 6 (dashed lines)). FIG. 1a) also shows that the equilibrium cis/trans ratio of 6,10-dimethylundeca-5,9-dien-2-one is between 60 and 65% E/(E+Z).

FIG. 1b) shows the stability behaviour. The x-axis represents again the time of heating, i.e. time of isomerization at 140° C., and the y-axis represents the purity ("P" in %) of the isomers to be isomerized and is measured by GC. Deviation from 100% means that one or more side products have been formed. FIG. 1b) shows that the polythiols have significantly better stability behaviour than the monothiols.

In a second series of experiments the isomers of 6,10-dimethylundec-5-en-2-one have been separated by distillation. The E-isomer has been isolated as having a content of (E)-6,10-dimethylundec-5-en-2-one of 95.5% (determined by GC) and the Z-isomer has been isolated in an enriched fraction having a content of (Z)-6,10-dimethylundec-5-en-2-one of 72.0% and a content of (E)-6,10-dimethylundeca-5,9-dien-2-one of 27.2% (total 99.2% isomers, determined by GC).

4,4'-Thiodibenzenethiol (3) have been added in different concentrations (1% by weight, 3% by weight and 3% by weight) to the E-isomer or Z-isomer, respectively. Then the mixture was stirred under argon and heated up to 140° C. and isomerized. The amount of E and Z isomers was measured by GC regularly after certain time of heating.

Figure 2A:
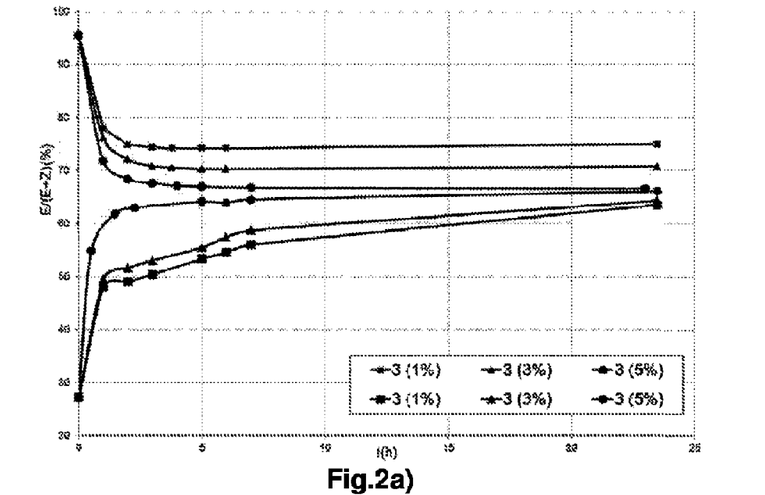
FIGS. 2a) and 3a) respectively show the results of isomerization according to second and third series of experiments in the Examples below.

FIG. 2a) shows the result of this isomerization experiments. The x-axis represents the time of heating, i.e. time of isomerization at 140° C., and the y-axis represents the percentage of E-isomer of the sum of isomers (E/(E+Z)) measured in the sample. For example a E/(E+Z) value of 80% represents a E/Z ratio of 80:20. FIG. 2a) shows the effect of different concentrations of polythiols: 1% ("3 (1%)"), 3% ("3 (3%)") and 5% ("3 (5%)"). The isomerization rate depends on the concentration used. Furthermore, the FIG. 2a) illustrates that that the equilibrium cis/trans ratio of 6,10-dimethylundec-5-en-2-one is at about 65% E/(E+Z).

In a third series of experiments the isomers of 6,10-dimethylundec-5-en-2-one have been separated by distillation. The E-isomer has been isolated as having a content of (E)-6,10-dimethylundec-5-en-2-one of 95.3% (determined by GC) and the Z-isomer has been isolated in an enriched fraction having a content of (Z)-6,10-dimethylundec-5-en-2-one of 75.8% and a content of (E)-6,10-dimethylundeca-5,9-dien-2-one of 23.4% (total 99.2% isomers, determined by GC).

Different amounts of polythiols were added to the E or Z isomer as indicated in table 2. Then the mixture was stirred and heated up to 140° C. under argon under which conditions isomerization took place. The amount of E and Z isomers was measured by GC regularly after certain reaction times.

TABLE 2

Figure 3A:
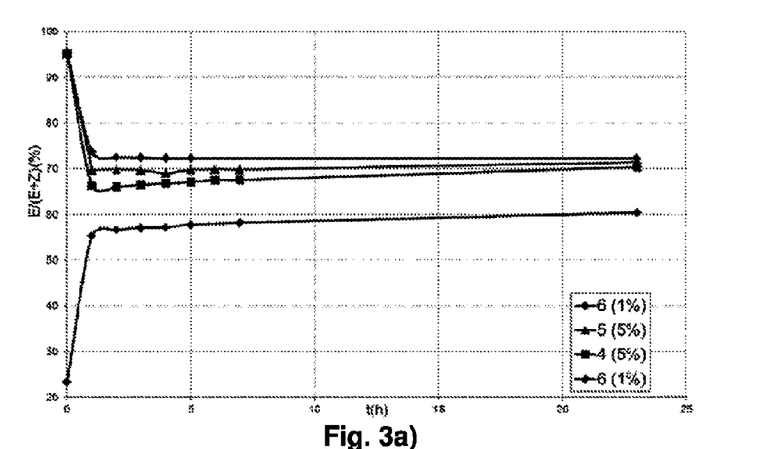

Catalysts used for the isomerization of of (E)- and (Z)-6,10-dimethylundec-5-en-2-one, respectively, in FIG. 3.

| Example | Catalyst | Concentration* |
|---|---|---|
| 4 | trimethylolpropane tris(mercaptoacetate) | 5% by weight |
| 5 | trimethylolpropane tri-(3-mercaptopropionate) | 5% by weight |
| 6 | pentaerythritol tetrakis (3-mercaptopropionate) | 1% by weight |

*concentration relative to ketone

FIG. 3a) shows the result of these isomerization experiments. The x-axis represents the time of heating, i.e. time of isomerization at 140° C., and the y-axis represents the percentage of E-isomer of the sum of isomers (E/(E+Z)) measured in the sample. For example a E/(E+Z) value of 80% represents a E/Z ratio of 80:20. FIG. 3a) shows that the equilibrium cis/trans ratio of 6,10-dimethylundec-5-en-2-one is between 60 and 70% E/(E+Z).

In a fourth series of experiments the isomers of 6,10,14-trimethylpentadec-5-en-2-one have been separated by distillation. The E-isomer has been isolated as having a content of (E)-6,10,14-trimethylpentadec-5-en-2-one of 96.3% (determined by GC) and the (Z)-6,10,14-trimethylpentadec-5-en-2-one has been isolated as having a E/Z ratio of 0.1:89.3 (at 89.4% purity, determined by GC).

5% by weight of pentaerythritol tetrakis (3-mercaptopropionate) was added to the E or Z isomer followed by a solvent where indicated in table 3. Then the mixture was stirred and heated up to 90° C. under argon under which conditions isomerization took place. The amount of the individual isomers was measured by GC regularly after certain reaction times.

TABLE 3

Figure 4A:
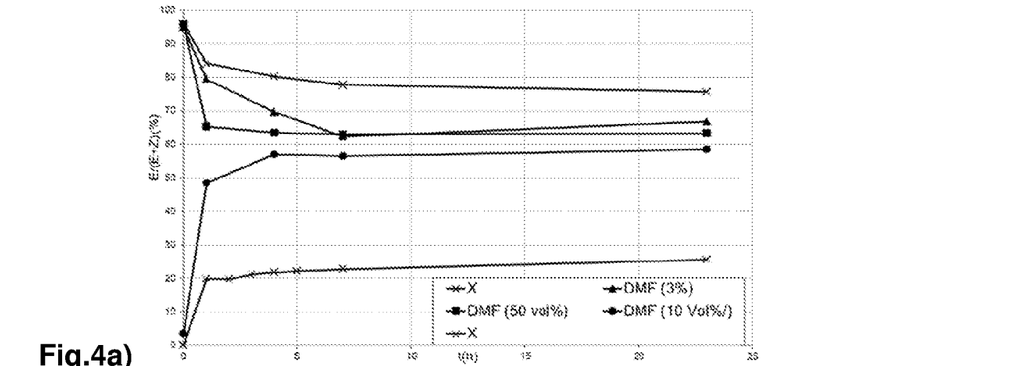
FIGS. 4a)-4c) respectively show the results of isomerization according to a fourth series of experiments in the Examples below.
Figure 4B:
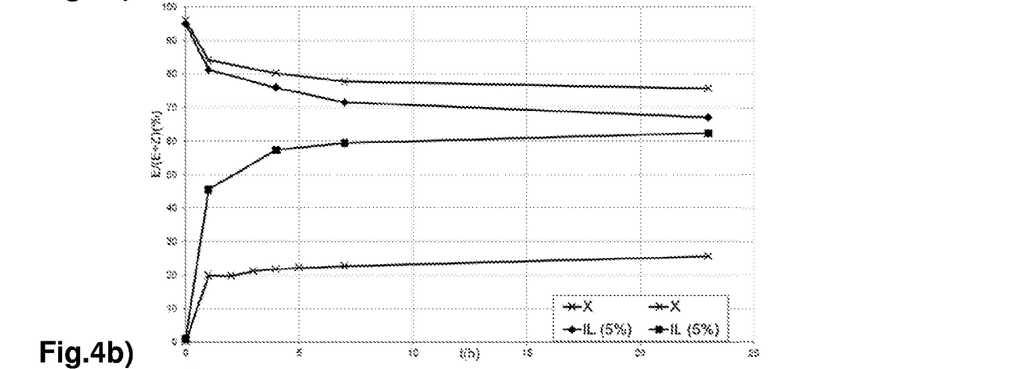
Figure 4C:
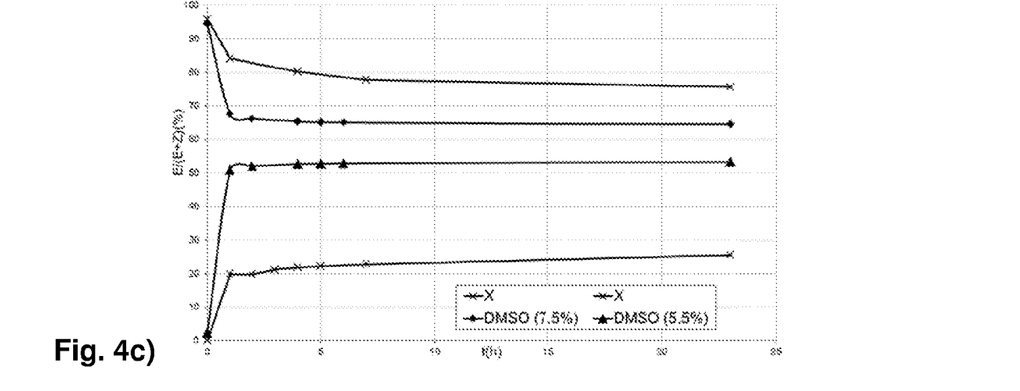

Effect of polar solvents on the isomerization efficiency of pentaerythritol tetrakis (3-mercaptopropionate) for (E)- and (Z)-6,10,14-trimethylpentadec-5-en-2-one in FIG. 4.

| Example | Solvent | Concentration* |
|---|---|---|
| X | None | — |
| DMF (3 vol. %) | N,N-dimethylformamide | 3% by volume |
| DMF (10 vol. %) | N,N-dimethylformamide | 10% by volume |
| DMF (50 vol. %) | N,N-dimethylformamide | 50% by volume |
| IL (5%) | Ionic liquid: 1-butyl-3-methylimidazolium bromide | 5% by weight |
| DMSO (5.5%) | dimethylsulfoxide | 5.5% by weight |
| DMSO (7.5%) | dimethylsulfoxide | 7.5% by weight |

*concentration of solvent in ketone.

FIGS. 4a)-c) show the result of these isomerization experiments. The x-axis represents the time of heating, i.e. time of isomerization at 90° C., and the y-axis represents the percentage of E-isomer of the sum of isomers (E/(E+Z))

measured in the sample. For example a E/(E+Z) value of 80% represents a E/Z ratio of 80:20. FIG. 4a) shows the accelerating effect of DMF onto the rate of isomerization. FIG. 4b) shows the accelerating effect of 1-butyl-3-methyl-imidazolium bromide, an ionic liquid, onto the rate of isomerization. FIG. 4c) shows the accelerating effect of DMSO onto the rate of isomerization.

The FIGS. 4a)-c) indicate that the equilibrium cis/trans ratio of (E/Z)-6,10,14-trimethylpentadec-5-en-2-one is around 60-63% E/(E+Z).

In a fifth series of experiments the isomers of 6,10,14-trimethylpentadeca-5,9,13-trien-2-one have been separated by distillation. The ZZ-isomer has been isolated as having a content of 88.6% of (5Z,9Z)-6,10,14-trimethylpentadeca-5,9,13-trien-2-one, 0% (5E,9E)-6,10,14-trimethylpentadeca-5,9,13-trien-2-one and 4.0% of the sum of (5E,9Z)- and (5Z,9E)-6,10,14-trimethylpentadeca-5,9,13-trien-2-one (total of 92.6% 6,10,14-trimethylpentadeca-5,9,13-trien-2-one isomers, measured by GC).

5% by weight of pentaerythritol tetrakis (3-mercaptopropionate) was added to the sample stated above. Then the mixture was stirred and heated up to 105° C. under argon under which conditions isomerization took place. The amount of the individual isomers was measured by GC regularly after certain reaction times.

Figure 5A:
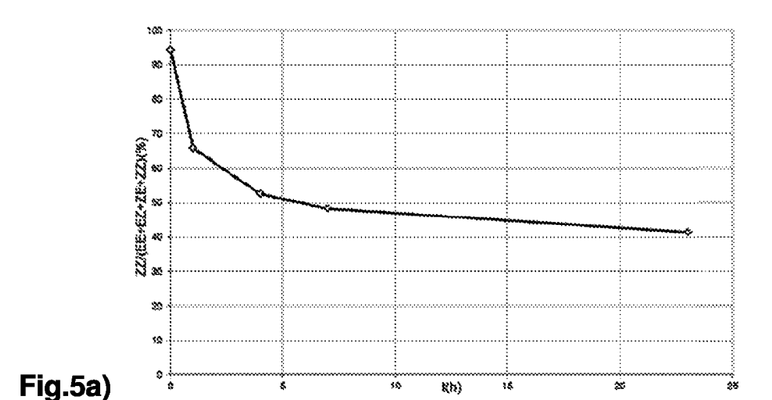
FIGS. 5a)-5c) respectively show the results of isomerization according to a fifth series of experiments in the Examples below.
Figure 5B:
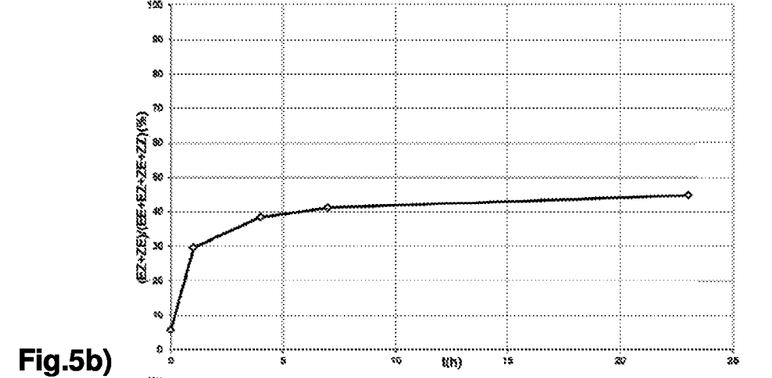
Figure 5C:
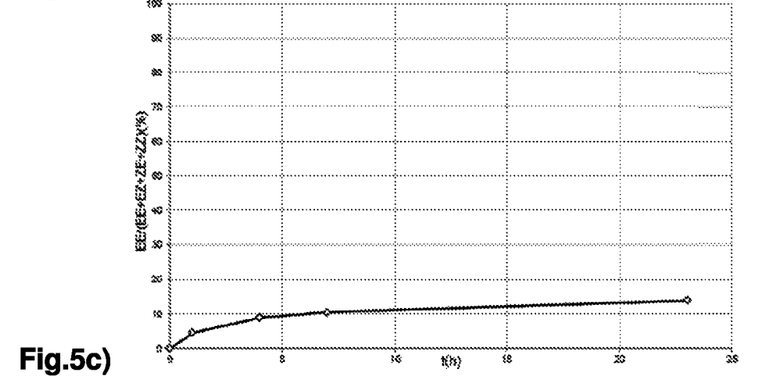

FIGS. 5a)-c) show the result of this isomerization experiment. The x-axis represents the time of heating, i.e. time of isomerization at 105° C., and the y-axis represents in FIG. 5a) the weight ratio of ZZ/(ZZ+EZ+ZE+EE). The y-axis represents in FIG. 5b) the weight ratio of (EZ+ZE)/(ZZ+EZ+ZE+EE). The y-axis represents in FIG. 5c) the weight ratio of EE/(ZZ+EZ+ZE+EE). FIGS. 5a)-c) show that all isomers are isomerized furnishing a ratio of isomers of about 40% ZZ/(ZZ+EZ+ZE+EE), about 46% (EZ+ZE)/(ZZ+EZ+ZE+EE) and about 14% EE/(ZZ+EZ+ZE+EE).

In a sixth series of experiments the isomers of 6,10,14-trimethylpentadeca-5,9-dien-2-one have been separated by distillation. The mixture of EZ- and ZE-isomers has been isolated as having a content of 93.3% of the sum of (5E,9Z)- and (5Z,9E)-6,10,14-trimethylpentadeca-5,9-dien-2-one, 3.0% (5E,9E)-6,10,14-trimethylpentadeca-5,9-dien-2-one and 1.0% of (5Z,9Z)-6,10,14-trimethylpentadeca-5,9-dien-2-one (total of 97.3% 6,10,14-trimethylpentadeca-5,9-dien-2-one isomers, measured by GC).

5% by weight of pentaerythritol tetrakis (3-mercaptopropionate) was added to the sample stated above. Then the mixture was stirred and heated up to 90° C. under argon under which conditions isomerization took place. The amount of the individual isomers was measured by GC regularly after certain reaction times.

Figure 6A:
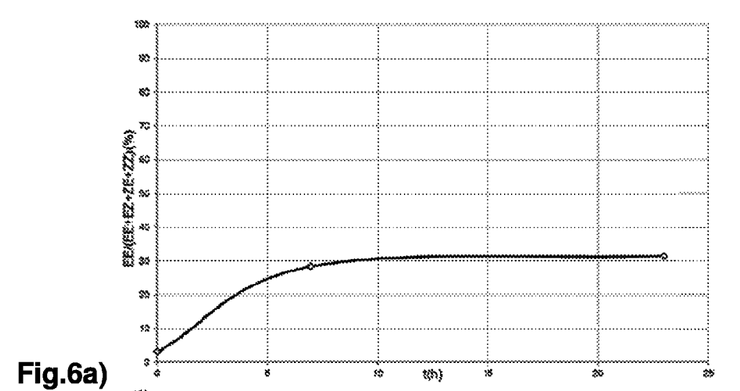
FIGS. 6a)-6c) respectively show the results of isomerization according to a sixth series of experiments in the Examples below.
Figure 6B:
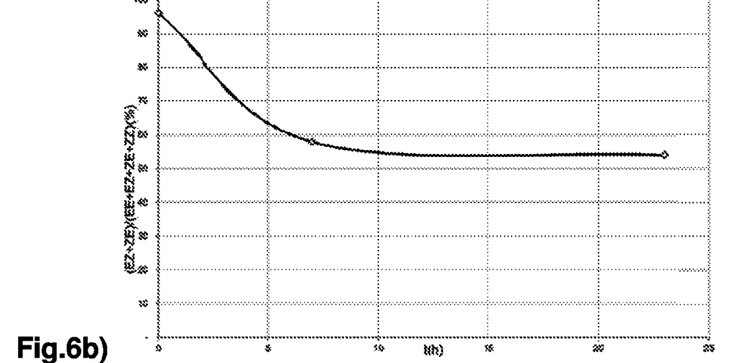
Figure 6C:
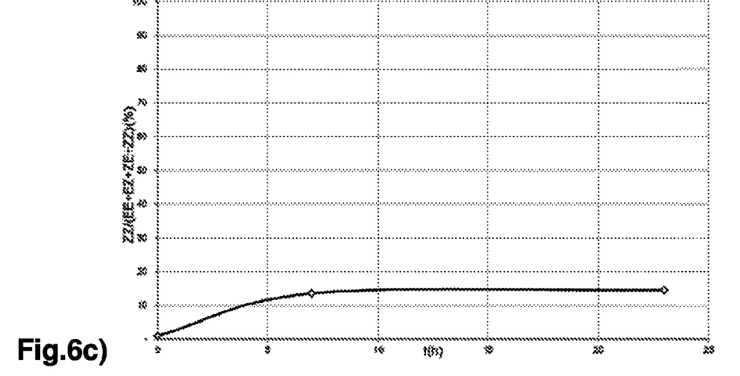

FIGS. 6a)-c) show the result of this isomerization experiment. The x-axis represents the time of heating, i.e. time of isomerization at 90° C., and the y-axis represents in FIG. 6a) the weight ratio of ZZ/(ZZ+EZ+ZE+EE). The y-axis represents in FIG. 6b) the weight ratio of (EZ+ZE)/(ZZ+EZ+ZE+EE). The y-axis represents in FIG. 6c) the weight ratio of EE/(ZZ+EZ+ZE+EE). FIGS. 6a)-c) show that all isomers are isomerized and an equilibrium is approached of about 15% ZZ/(ZZ+EZ+ZE+EE), about 54% (EZ+ZE)/(ZZ+EZ+ZE+EE) and about 31% EE/(ZZ+EZ+ZE+EE).

The invention claimed is:

1. A process for the cis/trans isomerization of an unsaturated compound A of formula (I) or (II) or an acetal or ketal thereof:

wherein Q stands for H or $CH_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration, and wherein the substructures in formula (I) and (II) represented by s1 and s2 can be in any sequence; and wherein the double bond having dotted lines (=====) in formula (I) and (II) represent either a single carbon-carbon bond or a double carbon-carbon bond; and wherein the symbol ✧ represents a stereogenic centre, wherein the process the steps of:

a) providing a cis or a trans isomer of the unsaturated compound A;

b) adding a polythiol to the cis or trans isomer of the unsaturated compound A provided according to step a) to form a mixture thereof; and c) heating the mixture of the polythiol and the cis or trans isomer of the unsaturated compound A to a temperature of between 20° C. and the boiling point of the unsaturated compound A in the presence of a polar solvent thereby leading to a mixture of cis/trans isomers of the unsaturated compound A.

2. The process according to claim 1, wherein the polythiol is present in an amount between 1 and 20% by weight relative to the amount of the unsaturated compound A.

3. The process according to claim 1, wherein the polythiol is a compound of formula (X):

wherein n1 represents an integer from 1 to 4, m1 represents an integer from 2 to 8, and A represents an aliphatic m1-valent hydrocarbon group of the molecular weight of between 28 g/mol and 400 g/mol.

4. A process for producing specific cis and trans isomers, respectively, from a mixture of cis and trans isomers of an unsaturated compound A of formula (I) or (II) or an acetal or ketal thereof:

wherein Q stands for H or $CH_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration, and wherein the substructures in formula (I) and (II) represented by s1 and s2 can be in any sequence; and wherein the double bond having dotted lines ( ===== ) in formula (I) and (II) represent either a single carbon-carbon bond or a double carbon-carbon bond; and wherein the symbol ✧ represents a stereogenic centre, wherein the process comprises the steps of:

i) providing a mixture of cis and trans isomers of the unsaturated compound A, wherein the cis isomers of the unsaturated compound A are present in the mixture in an amount by weight $w_{cis}$ and the trans isomers of the unsaturated compound A are present in the mixture in an amount by weight $w_{trans}$;

ii) adding a polythiol to the mixture of cis and trans isomers of the unsaturated compound A;

iii) heating the mixture of cis and trans isomers of the unsaturated compound A to a temperature $T_{iso1}$, which is the boiling point of an isomer $I_{lbp}$ which has a lowest boiling point of the mixture of cis and trans isomers of the unsaturated compound A provided according to step i);

iv) distilling off the isomer $I_{lbp}$ and collecting the isomer $I_{lbp}$;

v) conducting cis/trans isomerization of an isomer $I_{lbp}$ having a higher boiling point than the boiling point of the isomer $I_{lbp}$ in the presence of the polythiol added to the mixture according to step ii); and vi) after the step v), repeating the steps iii), iv) and v); and wherein the weight of the collected isomer $I_{lbp}$ is more than the weight $w_{cis}$ of the cis isomer of the unsaturated compound A in the mixture in the case where the collected isomer $I_{lbp}$ is a cis isomer of the unsaturated compound A; or the weight of the collected isomer $I_{lbp}$ is more than the weight $w_{trans}$ of the trans isomer of the unsaturated compound A in the mixture in the case where the collected isomer $I_{lbp}$ is a trans isomer of the unsaturated compound A; and wherein each of the weight $w_{cis}$ and weight $w_{trans}$ of the cis and trans isomers of the unsaturated compound A, respectively, in the mixture is 0 gram to 10 tons, with the proviso that the ratio of the weight $w_{cis}$ and the weight $w_{trans}$ is larger than 70/30 or smaller than 30/70 with the proviso that not both $w_{cis}$ and $w_{trans}$ are 0 grams.

5. The process of claim 4, wherein the weight of the collected isomer $I_{lbp}$ isomer is more than 80% by weight, of a sum of the weight $w_{trans}$ and the weight $w_{cis}$.

6. A process for producing specific cis and trans isomers, respectively, from a mixture of cis and trans isomers of an unsaturated compound A of formula (I) or (II) or an acetal or ketal thereof:

wherein Q stands for H or $CH_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration, and wherein the substructures in formula (I) and (II) represented by s1 and s2 can be in any sequence; and wherein the double bond having dotted lines ( ===== ) in formula (I) and (II) represent either a single carbon-carbon bond or a double carbon-carbon bond; and wherein the symbol ✧ represents a stereogenic centre, wherein the process comprises the steps of:

a) providing a mixture of cis and trans isomers of the unsaturated compound A, wherein the cis isomers of the unsaturated compound A are present in the mixture in an amount by weight $w_{cis}$ and the trans isomers of the unsaturated compound A are present in the mixture in an amount by weight $w_{trans}$;

b) adding a polythiol to the mixture of cis and trans isomers of the unsaturated compound A;

c) heating the mixture of cis and trans isomers of the unsaturated compound A to a temperature $T_{iso1}$, which is the boiling point of an isomer $I_{lbp}$ which has a lowest boiling point of the mixture of cis and trans isomers of the unsaturated compound A provided according to step i);

d) distilling off the isomer $I_{lbp}$;

e) isolating a specific isomer $I_{lbp}$ which has a higher boiling point than the boiling point of the isomer $I_{lbp}$ from a remainder of step d) and collecting the isomer $I_{hbp}$;

f) conducting cis/trans isomerization of the isomer $I_{lbp}$ and the remainder of step e) in the case there is a remainder after step e) in the presence of the polythiol added according to step b); and g) after the step f), repeating the steps c), d), e) and f), wherein the weight of the collected isomer $I_{hbp}$ is more than the weight $w_{cis}$ of the cis isomer of the unsaturated com- pound A in the mixture in the case where the collected isomer $I_{hbp}$ is a cis isomer of the unsaturated compound A; or the weight of the collected isomer $I_{hbp}$ is more than the weight $w_{trans}$ of the trans isomer of the unsaturated compound A in the mixture in the case where the collected isomer $I_{hbp}$ is a trans isomer of the unsaturated compound A; and wherein each of the weight $w_{cis}$ and weight $w_{trans}$ of the cis and trans isomers of the unsaturated compound A, respectively, in the mixture is 0 gram to 10 tons, with the proviso that the ratio of the weight $w_{cis}$ and the weight $w_{trans}$ is larger than 70/30 or smaller than 30/70 with the proviso that not both $w_{cis}$ and $w_{trans}$ are 0 grams.

7. The process according to claim 4 or 6, wherein the cis/trans isomerization is undertaken in the presence of a polar solvent.

8. The process according to claim 4 or 6, wherein the polythiol is a compound of formula (X):

wherein n1 represents an integer from 1 to 4,
m1 represents an integer from 2 to 8, and
A represents an aliphatic m1-valent hydrocarbon group of the molecular weight of between 28 g/mol and 400 g/mol.

9. The process according to claim 7, wherein the polar solvent is an ionic liquid.

10. The process according to claim 9, wherein the ionic liquid is at least one selected from the group consisting of 1-butyl-3-methylimidazolium bromide, N,N-dimethylformide (DMF), N-methyl-2-pyrrolidone (NMP) and dimethylsulphoxide (DMSO).

11. The process according to claim 1, wherein the polar solvent is an ionic liquid.

12. The process according to claim 11, wherein the ionic liquid is at least one selected from the group consisting of 1-butyl-3-methylimidazolium bromide, N,N-dimethylformide (DMF), N-methyl-2-pyrrolidone (NMP) and dimethylsulphoxide (DMSO).

13. The process according to claim 3, wherein n1 is 2, m1 is an integer from 3 or 4, and A represents an aliphatic m1-valent hydrocarbon group of the molecular weight of between 90 g/mol and 150 g/mol.

14. The process according to claim 8, wherein n1 is 2, m1 is an integer from 3 or 4, and A represents an aliphatic m1-valent hydrocarbon group of the molecular weight of between 90 g/mol and 150 g/mol.

15. The process according to claim 1, wherein the unsaturated compound A is an unsaturated ketal or an unsaturated acetal which is selected from the group consisting of 2-(4,8-dimethylnona-3,7-dien-1-yl)-2,5,5-trimethyl-1,3-dioxane, 2,6-dimethyl-10,10-bis(2,2,2-trifluoroethoxy)undeca-2,6-diene, 2-(4,8-dimethylnon-3-en-1-yl)-2,5,5-trimethyl-1,3-dioxane, 6,10-dimethyl-2,2-bis(2,2,2-trifluoro-ethoxy)undec-5-ene, 2,5,5-trimethyl-2-(4,8,12-trimethyltridec-3-en-1-yl)-1,3-dioxane, 6,10,14-trimethyl-2,2-bis(2,2,2-trifluoroethoxy)pentadec 5-ene, 2,5,5-trimethyl-2-(4,8,12-trimethyltrideca-3,7,11-trien-1-yl)-1,3-dioxane, 2,6,10-trimethyl-14,14-bis(2,2,2-trifluoroethoxy)pentadeca-2,6,10-triene, 2,5,5-trimethyl-2-(4,8,12-trimethyltrideca-3,7-dien-1-yl)-1,3-dioxane, 6,10,14-trimethyl-2,2-bis(2,2,2-trifluoroethoxy)pentadeca-5,9-diene, 2-(2,6-dimethylhept-1-en-1-yl)-5,5-dimethyl-1,3-dioxane, 3,7-dimethyl-1,1-bis(2,2,2-trifluoroethoxy)oct-2-ene, 3,7-dimethyl-1,1-bis(2,2,2-trifluoroethoxy)octa-2,6-diene, 2,6-dimethyl-8,8-bis(2,2,2-trifluoroethoxy)oct-2-ene, 2-(4,8-dimethylnona-1,3,7-trien-1-yl)-2,5,5-trimethyl-1,3-dioxane, 2,6-dimethyl-10,10-bis(2,2,2-trifluoroethoxy)undeca-2,6,8-triene, 2,5-dimethyl-2-(4,8,12-trimethyltridec-3-en-1-yl)-1,3-dioxane, 6,10,14 trimethyl 2,2 bis(2,2,2 trifluoroethoxy)pentadec 5 ene and E/Z-isomers thereof.

16. A process for the cis/trans isomerization of an unsaturated compound A of formula (I) or (II) or an acetal or ketal thereof:

wherein Q stands for H or $CH_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration, and wherein the substructures in formula (I) and (II) represented by s1 and s2 can be in any sequence; and wherein the double bond having dotted lines ( ------- ) in formula (I) and (II) represent either a single carbon-carbon bond or a double carbon-carbon bond; and wherein the symbol ✧ represents a stereogenic centre, wherein the process comprises the steps of:

a) providing a cis or a trans isomer of the unsaturated compound A;

b) adding a polythiol selected from the group consisting of 4,4'-dimercaptobiphenyl and 4,4'-thiodibenzenethiol to the cis or trans isomer of the unsaturated compound A provided according to step a) to form a mixture thereof; and c) heating the mixture of the polythiol and the cis or trans isomer of the unsaturated compound A to a temperature of between 20° C. and the boiling point of the unsaturated compound A thereby leading to a mixture of cis/trans isomers of the unsaturated compound A.

17. The process according to claim 16, wherein the unsaturated compound A is an unsaturated ketal or an unsaturated acetal.

18. The process according to claim 16, wherein the polythiol is present in an amount between 1 and 20% by weight relative to the amount of the unsaturated compound A.

19. The process according to claim 16, wherein the cis/trans isomerization is undertaken in the presence of a polar solvent.

20. The process according to claim 19, wherein the polar solvent is an ionic liquid.

21. The process according to claim 20, wherein the ionic liquid is at least one selected from the group consisting of 1-butyl-3-methylimidazolium bromide, N,N-dimethylformide (DMF), N-methyl-2-pyrrolidone (NMP) and dimethylsulphoxide (DMSO).

22. The process according to claim 1, wherein the unsaturated compound A is an unsaturated ketal or an unsaturated acetal selected from the group consisting of (R)-2,5,5-trimethyl-2-(4,8,12-trimethyltridec-3-en-1-yl)-1,3-dioxane, (R)-6,10,14-trimethyl-2,2-bis(2,2,2-trifluoroethoxy)pentadec-5-ene, (R)-2,6-dimethyl-8,8-bis(2,2,2-trifluoroethoxy)oct-2-ene, (R)-2,5-dimethyl-2-(4,8,12-trimethyltridec-3-en-1-yl)-1,3-dioxane and (R)-6,10,14-trimethyl-2,2-bis(2,2,2-trifluoroethoxy)pentadec-5-ene.

* * * * *